US006720003B2

(12) United States Patent
Chen et al.

(10) Patent No.: US 6,720,003 B2
(45) Date of Patent: Apr. 13, 2004

(54) SEROTONIN REUPTAKE INHIBITOR FORMULATIONS

(75) Inventors: Chih-Ming Chen, Davie, FL (US); Boyong Li, Davie, FL (US); Janice Cacace, Miami, FL (US)

(73) Assignee: Andrx Corporation, Davie, FL (US)

( * ) Notice: Subject to any disclaimer, the term of this patent is extended or adjusted under 35 U.S.C. 154(b) by 80 days.

(21) Appl. No.: 09/785,040

(22) Filed: Feb. 16, 2001

(65) Prior Publication Data

US 2002/0156066 A1 Oct. 24, 2002

(51) Int. Cl.$^7$ ................................................. A61K 9/20
(52) U.S. Cl. ....................... 424/464; 424/400; 424/465; 424/489; 514/321; 514/646
(58) Field of Search ......................... 514/321, 646; 424/465, 464, 486

(56) References Cited

U.S. PATENT DOCUMENTS

| | | | |
|---|---|---|---|
| 4,007,196 A | 2/1977 | Christensen et al. | 546/197 |
| 4,356,518 A | 10/1982 | Lemoine et al. | 360/51 |
| 4,721,723 A | 1/1988 | Barnes et al. | 514/321 |
| 4,772,288 A | 9/1988 | Borner et al. | 8/94.11 |
| 4,839,104 A | 6/1989 | Quallich et al. | 552/299 |
| 4,839,177 A | 6/1989 | Colombo et al. | 424/482 |
| 4,855,500 A | 8/1989 | Spavins | 564/270 |
| 5,082,970 A | 1/1992 | Braish | 564/424 |
| 5,196,607 A | 3/1993 | Quallich | 568/327 |
| 5,248,699 A | 9/1993 | Sysko et al. | 514/647 |
| 5,422,116 A | 6/1995 | Yen et al. | 424/427 |
| 5,422,123 A | 6/1995 | Conte et al. | 424/479 |
| 5,463,126 A | 10/1995 | Williams | 564/222 |
| 5,670,168 A | 9/1997 | Baichwal et al. | 424/464 |
| 5,672,612 A | 9/1997 | Ronsen et al. | 514/338 |
| 5,681,962 A | 10/1997 | Callander | 546/219 |
| 5,734,083 A | 3/1998 | Wilson et al. | 564/308 |
| 5,750,794 A | 5/1998 | Quallich | 548/322 |
| 5,811,436 A | 9/1998 | Leonard et al. | 514/321 |
| 5,856,493 A | 1/1999 | Ward et al. | 546/197 |
| 5,872,132 A | 2/1999 | Ward et al. | 514/321 |
| 5,874,447 A | 2/1999 | Benneker et al. | 514/321 |
| 5,900,423 A | 5/1999 | Ward et al. | 514/321 |
| 5,955,475 A | 9/1999 | Krape et al. | 514/321 |
| 6,168,805 B1 * | 1/2001 | Hein, II et al. | 424/465 |
| 6,395,300 B1 * | 5/2002 | Straub et al. | 424/489 |

FOREIGN PATENT DOCUMENTS

| | | | | |
|---|---|---|---|---|
| WO | 9900131 | 1/1999 | | A61K/31/445 |
| WO | 9926625 | 6/1999 | | A61K/31/445 |
| WO | 9956751 | 11/1999 | | A61K/31/445 |

OTHER PUBLICATIONS

*Psychopharmacology* 57, 1515–1530 (1978).
*Acta. Pharmacol. Et Toxicol.* 44, 289–295 (1979).

* cited by examiner

*Primary Examiner*—Thurman K. Page
*Assistant Examiner*—Robert M DeWitty
(74) *Attorney, Agent, or Firm*—Davidson, Davidson & Kappel, LLC

(57) ABSTRACT

A process for preparing amorphous paroxetine hydrochloride or sertraline hydrochloride is provided, which comprises preparing a solution in which paroxetine hydrochloride or sertraline hydrochloride and a water-soluble polymer are dissolved in a co-solvent of a volatile organic solvent and water. Said solution is dried to obtain a composition comprising amorphous paroxetine hydrochloride or sertraline hydrochloride and the water-soluble matrix.

46 Claims, No Drawings

SEROTONIN REUPTAKE INHIBITOR FORMULATIONS

FIELD OF THE INVENTION

The present invention is related to processes for preparing solid dispersions comprising paroxetine or sertraline dispersed in a water-soluble polymer, and preparation of solid oral dosage forms containing the dispersions. The present invention is also related to processes for preparing an amorphous paroxetine salt or sertraline salt, and incorporation of these amorphous drugs into suitable pharmaceutical dosage forms.

BACKGROUND OF THE INVENTION

Paroxetine and sertraline are two of the compounds having anti-depressant properties that are known as selective serotonin reuptake inhibitors ("SSRI").

Of these, paroxetine, the chemical name of which is (−)-trans-4R-(4'-fluorophenyl)-3S-[(3'4'-methylenedioxyphenoxy)methyl]-piperidine, has been identified in the art as having utility in the treatment of a variety of disease states, including but not limited to depression, anxiety, obsessive compulsive disorders, panic, pain, obesity, senile dementia, migraine, bulimia, anorexia, alcoholism, trichotillomania, dysthymnia, substance abuse, social phobia, depression arising from pre-menstrual tension or adolescence, and premature ejaculation. Paroxetine is indicated for the treatment of depression, obsessive compulsive disorder and panic disorder with or without agoraphobia in a recommended dose of 10 to 60 mg once a day. The antidepressant action of paroxetine and its efficacy in the treatment of obsessive compulsive disorder and panic disorder is presumed to be linked to potentiation of serotonergic activity in the central nervous system resulting from inhibition of neuronal reuptake of serotonin. Generally speaking, paroxetine hydrochloride is a moderately water-soluble, orally administered antidepressant having a melting point range of 120° to 138° C. and a solubility of 5.4 mg/ml in water. Paroxetine is commercially available in the form of paroxetine hydrochloride hemihydrate, marketed under the name Paxil®(SmithKline Beecham).

Because of its basicity, it has been considered preferable that paroxetine be prepared in the form of an acid addition salt. However, most of the known salts of paroxetine are considered to have unsuitable physico-chemical properties for ensuring safe and efficient handling during production of the final product, since they are unstable and possess undesirable hygroscopicity. Furthermore, their formation by crystallization from both aqueous or non-aqueous solvents provides a low yield.

A number of patents have addressed the preparation of paroxetine. For example, U.S. Pat. No. 4,007,196 (Christensen, et al.) describes the preparation of paroxetine as a free base with the subsequent conversion to the maleic acid salt. The use of the acetate salt of paroxetine is also known, e.g., from *Psychopharmacology* 57, 1515–153 (1978). The limited use of the hydrochloride salt of paroxetine in an aqueous solution has also been described, e.g., in *Acta. Phamacol. et Toxicol.* 44,289–295 (1979). U.S. Pat. No. 4,721,723 (Barnes et al.) describes crystalline paroxetine hydrochloride hemihydrate, compositions containing the same and processes for its preparation. However, the processes described in the Barnes patent require post-synthetic treatment of the product in order to obtain the crystalline form, which adds to the difficulty and overall cost of production.

U.S. Pat. No. 5,681,962 (Callander) describes a process for preparing paroxetine, and in particular the hydrochloride hemi-hydrate form of paroxetine, using diborane as a reducing agent.

U.S. Pat. Nos. 5,856,493, 5,900,423 and 5,872,132 (each to Ward et al.) describe paroxetine hydrochloride anhydrate which is substantially free of propan-2-ol and methods of preparing the same, which are stated to overcome problems described in the art by removing the solvent from the paroxetine salt. The preparation of the paroxetine hydrochloride anhydrate substantially free of propan-2-ol is said to comprise crystallizing paroxetine hydrochloride in either (I) an organic solvent which forms a solvate with the paroxetine hydrochloride and which is not removable by conventional drying techniques (e.g., alcohols such as ethanol); or (II) an organic solvent which does or does not form a solvate with the paroxetine hydrochloride but which are removable by conventional vacuum oven drying; and thereafter in the case of (I) displacing the solvated solvent using a displacing agent (e.g., water) or in the case of (II) removing the solvent.

U.S. Pat. No. 5,874,447 (Benneker, et al.) describes the preparation of paroxetine sulfonates which are said to exhibit high solubility. According to the method of that patent, paroxetine (or a salt and/or base thereof) is mixed together with a sulfonic acid to form a solution, followed by the separation of the resultant paroxetine sulfonate from this solution. The resultant sulfonate is further said to be useful as a reagent in further syntheses, e.g., as a start reagent for forming further acid addition salts.

Amorphous forms of paroxetine have also been reported. For example, U.S. Pat. No. 4,721,723 (Barnes et al.), in distinguishing the hemihydrate salt form of paroxetine disclosed therein from other forms of paroxetine, reports that such hemihydrate form is desirable because amorphous paroxetine hydrochloride is undesirably hygroscopic and has poor handling qualities.

U.S. Pat. No. 5,672,612 (Ronsen et al.) describes amorphous paroxetine hydrochloride ethanol composition which is purported to be substantially non-hydroscopic and free-flowing. Said composition is prepared by dissolving paroxetine free base in a hydrochloric acid-ethanol solution followed by drying.

U.S. Pat. No. 5,955,475 (Krape et al.) describes processes for preparing a solid dispersion of an anhydrate form of a paroxetine salt. The processes use the free base of paroxetine, an oil, which is said to allow the solid dispersion to be prepared at a low temperature via a fusion process or with decreased organic solvent volumes via a solvent process, and the formation of a paroxetine salt during the solid dispersion manufacture process. Thus, in a first embodiment, Krape, et al. describe a process wherein a solution is formed of a water soluble polymeric carrier (e.g., polyethylene glycol or polyvinylpyrrolidone) and a non-aqueous solvent (e.g., an alcohol such as ethanol); dissolving paroxetine free base into the solution, wherein the ratio of polymeric carrier to paroxetine is 4:1 to 1:1, by weight; contacting the paroxetine free base in solution with at least one equivalent of an acid (hydrogen chloride in the form of dry hydrogen chloride gas or dry hydrogen chloride dissolved into a non-aqueous solvent) to form a paroxetine salt in solution (paroxetine hydrogen chloride); and then removing the non-aqueous solvent by evaporation under vacuum. A second embodiment is described wherein the paroxetine free base is dissolved into the solution of polymeric carrier and non-aqueous solvent to form a mixture having the aforementioned ratio of polymeric carrier to paroxetine free base, and thereafter the mixture is heated to form a molten homogeneous melt of polymeric carrier and paroxetine free base. Thereafter, the molten homogeneous melt of polymeric carrier and paroxetine free base is contacted with at least one equivalent of dry hydrogen chloride to form paroxetine hydrogen chloride in the molten homogeneous melt, and the molten homogeneous melt is then cooled to form a water soluble solid state dispersion of an anhydrate form of paroxetine hydrochloride.

PCT International Application No. WO99/56751 (Hein et al.) describes a process for preparing an amorphous form of paroxetine. The process involves mixing of paroxetine base or salt with water and a polymer, and drying said mixture. This aqueous solvent process purportedly provides an amorphous solid form of paroxetine. Due to the low solubility of paroxetine, however, heating of paroxetine solution to 60° C. is required in this process to prevent recrystallization of a paroxetine salt, especially at higher concentrations, which is inconvenient and may subject the drug to decomposition. In addition, use of water as the solvent might render the drying step more difficult, especially when large quantities of the drug solution are involved.

Like paroxetine, sertraline, also known as (1S-cis)-4-(3,4-dichlorophenyl)-1,2,3-4-tetrahydro-N-methyl-1-naphthalenamine, is a selective serotonin reuptake inhibitor. Sertraline is commercially available as sertraline hydrochloride, under the trademark Zoloft (Pfizer). Sertraline is indicated for treatment of depression, obsessive-compulsive disorder and panic disorder.

U.S. Pat. No. 4,356,518, describes sertraline, its salts and derivatives, and process for preparing the same. U.S. Pat. Nos. 4,772,288; 4,839,104; 4,855,500; 5,082,970; 5,196,607; 5,463,126; 5,422,116; and 5,750,794, each of these patents, also describe various processes for preparing sertraline.

Sertraline salts, like those of paroxetine, are reported to exist in different polymorphic forms. For example, U.S. Pat. No. 5,248,699 reports allegedly novel polymorphic forms of sertraline hydrochloride, designated as Forms I to V, which are described as being different from each other in their physical properties, stability, spectral data and methods of preparation.

U.S. Pat. No. 5,734,083 also provides a purportedly novel polymorphic form of sertraline hydrochloride, form T1, and methods of preparation.

OBJECTS AND SUMMARY OF THE INVENTION

It is an object of the invention to provide a process for preparing a solid dispersion comprising a compound that is a selective serotonin reuptake inhibitor having antidepressant properties, such as paroxetine or sertraline, wherein the compound is dispersed in a water-soluble polymer.

It is an object of the invention to provide a process for obtaining an amorphous paroxetine salt or sertraline salt, and pharmaceutical formulations containing the same.

It is an object of the invention to provide a process for preparing substantially non-hygroscopic amorphous paroxetine hydrochloride or amorphous sertraline hydrochloride.

It is a further object of the invention to provide a process for preparing amorphous paroxetine hydrochloride or amorphous sertraline hydrochloride having good handling properties, which can be formulated into pharmaceutically acceptable formulations for oral administration.

In accordance with the above-mentioned objects and others, the invention is related in part to a process for preparing an amorphous (non-crystalline) form of paroxetine hydrochloride or sertraline hydrochloride. The process comprises preparing a solution in which paroxetine hydrochloride or sertraline hydrochloride, along with a water-soluble polymer, is dissolved in a co-solvent of a volatile organic solvent and water. The solution is then dried to produce a composition comprising an amorphous form of paroxetine hydrochloride or sertraline hydrochloride and the water-soluble polymer. In preferred embodiments, the composition comprises a solid dispersion, wherein the amorphous paroxetine hydrochloride or sertraline hydrochloride is dispersed in the water-soluble polymer. The composition containing the amorphous drug and the water-soluble polymer may then be further processed into pharmaceutically acceptable dosage forms.

In certain preferred embodiments of the invention, the weight ratio of the volatile organic solvent to water in the co-solvent is from about 95:5 to about 60:40, more preferably from about 80:20 to about 70:30. Preferably, the volatile organic solvent is selected from the group consisting of methanol, ethanol, isopropyl alcohol and mixtures thereof, with methanol being the most preferred.

In certain preferred embodiments of the invention, the weight ratio of the paroxetine hydrochloride or sertraline hydrochloride to the water-soluble polymer is not greater than about 1:4, more preferably from about 1:1 to about 1:4, most preferably about 1:2.

In certain embodiments, the concentration of the paroxetine hydrochloride or sertraline hydrochloride in the solution containing the drug and the water-soluble polymer is from about 2 to about 30%, preferably from about 5 to about 25%, by weight.

In certain embodiments, the concentration of the water-soluble polymer in the solution containing the drug and the polymer is no greater than about 30%, more preferably about 20%.

In certain embodiments, the solution containing paroxetine hydrochloride or sertraline hydrochloride and the water-soluble polymer may be sprayed onto a pharmaceutically acceptable carrier (or substrate) and dried. Optionally, before the solution is sprayed onto the carrier, one or more additional pharmaceutical ingredients may be mixed into the solution e.g., for stabilization or to aid processing.

For example, the pharmaceutical carrier may comprise a plurality of particles of a material such as microcrystalline cellulose or calcium phosphate dibasic. In such embodiments, a granulate is formed via the spraying of the solution onto the carrier. Additional processing steps may then be undertaken to prepare a uniform granulate suitable for incorporation into gelatin capsules in desired unit doses of the active ingredient. Such additional processing steps may further include the addition of pharmaceutically acceptable tableting excipients, with the resultant mixture being compressed into pharmaceutically acceptable tablets containing a desired unit dose of the drug.

Alternatively, the pharmaceutically acceptable carrier may comprise placebo tablets. A sufficient quantity of the amorphous paroxetine hydrochloride or sertraline hydrochloride solution is sprayed onto such placebo tablets to incorporate the desired unit dose of the active ingredient. Thereafter, the coated tablets may be further processed, for example, via overcoating with a film-coating containing a barrier agent (such as hydroxypropylmethylcellulose, acrylic polymers, ethylcellulose and the like) and/or a colorant.

The invention is also directed to a method of treating human patients, comprising administering effective amounts of the amorphous paroxetine hydrochloride or sertraline hydrochloride formulations prepared in accordance with the invention to human patients.

The invention is further related to a method of treating depression, obsessive compulsive disorder and/or panic disorder in humans comprising orally administering an effective dose of a pharmaceutically acceptable solid dispersion of amorphous paroxetine hydrochloride or sertraline hydrochloride prepared in accordance with the processes set forth herein.

The present invention is also directed to a process for preparing a solid dispersion comprising an active ingredient dispersed in a water-soluble polymer, the active ingredient being selected from the group consisting of paroxetine free base, a paroxetine salt, sertraline free base, a sertraline salt, and mixtures thereof. The process comprises preparing a solution in which the active ingredient and the water-soluble carrier are dissolved in a co-solvent of a volatile organic solvent and water, and drying said solution to produce a solid dispersion comprising the active ingredient dispersed in the water-soluble polymer.

The term "paroxetine," as used in the present invention, refers to paroxetine in a salt form or free base form. The "free base" form of paroxetine is a viscous oil at standard temperature and pressure whereas the "salt form" is the acid addition product of paroxetine.

The term "sertraline," as used in the present invention refers both to the free base form of sertraline as well as its salt form.

By "bioavailable" it is meant for purposes of the present invention that the paroxetine or sertraline is released from the formulation and becomes available in the body at the intended site of drug action.

DETAILED DESCRIPTION OF THE INVENTION

The present invention is in part directed to a process for preparing a solid dispersion comprising an active ingredient dispersed in a water-soluble polymer, the active ingredient being selected from the group consisting of paroxetine free base, a paroxetine salt, sertraline free base, a sertraline salt, and mixtures thereof. The process comprises preparing a solution in which the active ingredient and the water-soluble carrier are dissolved in a co-solvent of a volatile organic solvent and water, and drying said solution to produce a solid dispersion comprising the active ingredient dispersed in the water-soluble polymer.

In certain preferred embodiments of the invention, when the active ingredient is a paroxetine salt or sertraline salt, and the solid dispersion obtained from the processes of the present invention comprises an amorphous form of the active ingredient, one function the water-soluble polymer in the solution serves is to prevent recrystallization of the paroxetine or sertraline salt. Thus, the lower limit of polymer in the solution is that amount which prevents the paroxetine salt or sertraline salt from recrystallizing. The upper limit of polymer in the solution is such that the ratio of paroxetine or sertraline salt to the polymer is preferably not greater than about 1:4. One skilled in the art will appreciate that the amount of polymer added will be dependent upon factors such as the physical properties of the polymer, the processing conditions, and the intended final product. In certain preferred embodiments, when the active ingredient is a paroxetine or sertraline salt, the drug:polymer ratio is from about 1:1 to about 1:4, and most preferably about 1:2.

In certain preferred embodiments, the active ingredient comprises a paroxetine salt or a sertraline salt, and the solid dispersion produced by the process comprises an amorphous form of the active ingredient dispersed in a water-soluble polymer.

The order in which the ingredients (e.g., active ingredient, the water-soluble polymer, the volatile organic solvent, water) are added in preparing the solution containing the active ingredient and the water-soluble polymer may be varied. Preferably, the solution containing the drug and the water-soluble polymer in the co-solvent may be prepared at ambient temperature (without heating) and pressure, e.g., by stirring the mixture containing the ingredients until a clear solution is obtained. The solution is subsequently dried to produce the solid dispersion, wherein the active ingredient is dispersed in the water-soluble carrier.

In certain embodiments of the invention, the solution containing the acid addition salt of paroxetine or sertraline and the water-soluble polymer is prepared by adding acid in water (e.g., 1N HCl) to a solution in which paroxetine or sertraline free base is dissolved in the volatile organic solvent (e.g., methanol). The acid is added in a sufficient amount to ensure conversion of the paroxetine or sertraline free base to the corresponding acid addition salt thereof (e.g., at least the stoichiometric amount of the acid, preferably more than the stoichiometric amount). This step results in a solution of the acid addition salt of paroxetine or sertraline in the co-solvent of the volatile organic solvent and water. Subsequently, the water-soluble polymer is added to said solution to obtain the solution in which the active ingredient and the water-soluble polymer are dissolved in the co-solvent, which may then be dried to obtain the solid dispersion of the amorphous acid addition salt of paroxetine or sertraline.

In certain preferred embodiments, the process of preparing the solution of the acid addition salt of paroxetine or sertraline and the water-soluble polymer may start with the salt form of the drug, rather than the free base form, followed by addition of the acid. For example, paroxetine hydrochloride is dissolved in the co-solvent of a volatile organic solvent (e.g., methanol) and water. An excess amount of hydrochloric acid (e.g., hydrochloric acid diluted in water) may be added to this solution to stabilize paroxetine HCl in solution. A water-soluble polymer may be added to the same solvent along with the drug, or before or after the addition of the drug, to obtain the solution of the drug and the polymer.

Preferably, the paroxetine salt is paroxetine hydrochloride and the sertraline salt is sertraline hydrochloride. However, other salts of paroxetine and sertraline may also be used to prepare the solid dispersions according to the process of the present invention. As used in this application, the term "paroxetine salt" or "sertraline salt" refers to acid addition salts. Such salts include mineral or organic acid salts of the basic piperidine residue; and the like. Acceptable non-toxic salts include those derived from inorganic acids such as hydrobromic, sulfuric, sulamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethanesulfonic, ethanedisulfonic, oxalic, isethionic, and the like. Further suitable salts can be found in *Remington's Pharmaceutical Sciences*, 17$^{th}$ ed., Mack Publishing Co., Easton, Pa., 1985, p. 1418, which is incorporated herein by reference.

In certain embodiments, the concentration of the drug in the solution of the drug and the polymer is from about 2% to about 30%, by weight, more preferably from about 5% to about 25%.

Preferably, the concentration of the water-soluble polymer in the solution containing the active ingredient and the polymer is no greater than about 30%, more preferably about 20% by weight.

Suitable volatile organic solvent(s) useful in the processes of the invention are both capable of dissolving the active ingredient, as well as the water-soluble polymer, and are chemically inert with respect to both the active ingredient and the polymer. Examples of suitable volatile organic solvents include but are not limited to methanol, ethanol, propanol (including both n-propanol and i-propanol), butanol (including n-butanol, i-butanol, and s-butanol), toluene, benzene supercritical liquid $CO_2$, chloroform, methylene chloride, acetonitrile, ketones (e.g. dimethylketone, methylethylketone, and diethylketone), dimethylformamide, dimethylsulfoxide, esters (a non-limiting example being ethyl acetate), ethers (non-limiting examples being diethylether, dipropylether), 1,4-dioxane, tetrahydrofuran, pentanes, hexanes, heptanes, trichloroethene, and/or suitable mixtures thereof. In preferred embodiments, the volatile organic solvent is selected from the group consisting of methanol, ethanol, isopropyl alcohol and mixtures thereof, the most preferred volatile organic solvent being methanol.

In preferred embodiments of the present invention, suitable water-soluble polymers are selected from the group consisting of polyvinylpyrrolidone ("PVP"), hydroxypropylmethyl-cellulose ("HPMC"), polyethyleneglycol ("PEG") and mixtures thereof. When the polymer is PVP, it is preferred that the PVP has an average molecular weight from about 2000 to about 3 million, and more preferably from about 7,000 to about 1,500,000. Most preferred PVP has an average molecular weight of about 40,000 (such as Povidone K30) or about 1,500,000 (such as Povidone K90). Both Povidone K30 and K90 are commercially available from BASF, Midland, Mich. When the polymer is PEG, it is preferred that the PEG has an average molecular weight from about 1,000 to about 20,000. When the polymer is HPMC, low viscosity grades of HMPC, such as commercially available Methocel E5 or Methocel E3 LV (both available from Dow Chemical Co.), are preferred. In certain embodiments, the water-soluble polymer is Povidone K25.

Other suitable water soluble polymers include, but are not limited to, hydroxypropylcellulose, methyl cellulose, carboxymethyl cellulose, sodium carboxymethyl cellulose, cellulose acetate phthalate, cellulose acetate butyrate, hydroxyethyl cellulose, ethyl cellulose, polyvinyl alcohol, polypropylene, dextrans, dextrins, hydroxypropyl-beta-cyclodextrin, chitosan, copolymers of lactic and glycolic acid, lactic acid polymers, glycolic acid polymers, polyorthoesters, polyanyhydrides, polyvinyl chloride, polyvinyl acetate, ethylene vinyl acetate, lectins, carbopols, silicon elastomers, polyacrylic polymers, maltodextrins, and alpha-, beta-, and gamma-cyclodextrins, and suitable mixtures of the foregoing.

Once the solution containing both the active ingredient and the water soluble polymer in the co-solvent is prepared, the co-solvent is evaporated to dryness to obtain a co-precipitate of the active ingredient and the water soluble polymer, which is a solid dispersion comprising the active ingredient dispersed in the water-soluble polymer. In certain preferred embodiments, when the active ingredient is a paroxetine salt or sertraline salt, the solid dispersion obtained from the drying step comprises amorphous paroxetine or sertraline salt, e.g., amorphous paroxetine hydrochloride or sertraline hydrochloride.

In certain embodiments of the invention, before the co-solvent is removed, additional pharmaceutical excipients may be added to the solution of the active ingredient and the water-soluble polymer to obtain a mixture, e.g., to aid the processing or for stabilization. Such pharmaceutical excipients may include but are not limited to, for example, a surfactant (e.g., polysorbate 80), a stabilizer (e.g., hydrochloric acid or citric acid), an antioxidant, a glidant (e.g. talc or silicon dioxide), a diluent and/or mixtures thereof.

The stabilizer added to the solution containing the active ingredient and the water soluble polymer suitable in the present invention includes pharmaceutically acceptable inorganic acids and organic acids. Preferably, the stabilizer is the same acid as the acid addition portion of the active ingredients. The stabilizer can be added before or after the addition of active ingredient and the water soluble polymer. Preferably the stabilizer is added before the addition of active ingredient and the water soluble polymer.

The surfactant added to the solution containing the active ingredient and the water soluble polymer is chosen based partly on its compatibility with the other ingredients of the mixture, particularly the polymer. Suitable surfactants include pharmaceutically acceptable non-ionic surfactants, anionic surfactants, cationic surfactants, amphoteric (amphipathic/amphophilic) surfactants or mixtures thereof. Preferably, the surfactant is nonionic. Preferably, the surfactant when included in the drug/polymer solution comprises from about 0.05% to about 2% of the mixture, by weight, and more preferably from about 0.1% to about 1%, by weight.

In preferred embodiments, the removal of the co-solvent from the solution (or the mixture, when additional pharmaceutical excipient(s) are added to the solution) containing the active ingredient and the water soluble polymer, or from a mixture obtained by adding one or more additional pharmaceutical ingredients to the solution, may be carried out by, e.g., by spray drying the solution or mixture according to conventional techniques well known to those skilled in the art.

Once dried, the solid dispersion or "solid solution" comprising the active ingredient and the water-soluble polymer is obtained. A solid dispersion is defined as "the dispersion of one or more active ingredients in an inert carrier or matrix at solid-state prepared by the melting (fusion), solvent or melting-solvent method" (W. A. Chiou and R. Riegelman, J. Pharm. Sci., 60, 1281, 1971). Alternatively, Corrigan (O. I. Corrigan, Drug Dev. Inc. Pharm., 11, 697, 1985), has defined the solid dispersion as a "product formed by converting a fluid drug-carrier combination to the solid state." For practical purposes, the term "solid dispersion" has been considered synonymous with oral dosage forms, which usually contain a carrier having a higher water solubility than the medicament. For purposes of the present invention, term "solid dispersion" is considered to be interchangeable with the term "solid solution."

In certain embodiments, the solution or the mixture described above, which contains the active ingredient and the water soluble polymer, may be sprayed onto a pharmaceutically acceptable carrier and dried to produce a granulate containing the active ingredient and the water soluble polymer, preferably to a weight gain of from about 5% to about 500%, more preferably from about 10% to about 40%, and most preferably from about 50% to about 300%.

The pharmaceutically acceptable carrier may be a pharmaceutically acceptable carrier material selected from such materials known to those skilled in the art, for example, microcrystalline cellulose or calcium phosphate dibasic. Other suitable pharmaceutically acceptable carriers include, but are not limited to, calcium phosphate dihydrate, calcium sulfate dihydrate, cellulose derivatives, dextrose, lactose, anhydrous lactose, spray-dried lactose, lactose monohydrate, mannitol, starches, sorbitol and sucrose. Further examples of the carrier include hydroxypropylmethylcellulose, hydroxypropylcellulose, methyl cellulose, carboxymethyl cellulose, sodium carboxymethyl cellulose, polyvinylpyrrolidone, polyethyleneglycol, cellulose acetate butyrate, hydroxyethyl cellulose, ethyl cellulose, polyvinyl alcohol, polypropylene, dextrans, dextrins, hydroxypropyl-beta-cyclodextrin, chitosan, copolymers of lactic and glycolic acid, lactic acid polymers, glycolic acid polymers, polyorthoesters, polyanyhydrides, polyvinyl chloride, polyvinyl acetate, ethylene vinyl acetate, lectins, carbopols, silicon elastomers, polyacrylic polymers, maltodextrins, fructose, inositol, trehalose, maltose raffinose, and alpha-, beta-, and gamma-cyclodextrins, and suitable mixtures of the foregoing.

In certain embodiments, the drug:polymer solution or mixture may be sprayed onto a pharmaceutically acceptable carrier comprising multiparticulates (e.g., microcrystalline cellulose), preferably to a weight gain of from about 10% to about 400%, more preferably from about 50% to about 300%. The spray-drying procedure may be carried out in a fluid-bed processor with a Wuster apparatus at a suitable temperature and spray rate to form granules, e.g., at a temperature of about 40–50° C. and a spray rate of about 40–120 ml/min. Next, the granules are preferably milled, e.g., by being passed through a mesh screen, e.g., a 16, 20 or 30 mesh stainless steel screen. It is preferred that the spray drying of the solution (or the mixture) results in a homogenous solid dispersion which is substantially free of the solvents. For purposes of the present invention, substantially free means that the solid dispersion contains less than 20% by weight of residual solvent, more preferably less than 5%, and most preferably less than 3%.

Alternatively, the paroxetine hydrochloride-polymer solution (or mixture) may be spray-dried onto a placebo tablet, which may result in the weight gain of from about 5% to about 500%.

Once the co-solvent is evaporated from the solution (or mixture) containing the active ingredient and a water-soluble polymer, the solid dispersion of the drug is obtained, which may be formulated into suitable oral dosage forms, including tablets or capsules.

If the solid dispersion is prepared as a granulate, such granulate may then be blended with other excipients and compressed into tablets.

When the granulate is to be tableted, it is preferably admixed with suitable amounts of one or more pharmaceutically acceptable excipients, including but not limited to disintegrants such as cross-linked polyvinylpyrrolidone and sodium starch glycolate; fillers such as microcrystalline cellulose, lactose, calcium phosphate dibasic, and the like; glidants such as talc and silicon dioxide; lubricants such as magnesium stearate and acetylated monoglycerides; binders; coloring agents; flavoring agents; stabilizers such as citric acid or alginic acid; and/or preservatives.

Sufficient quantities of pharmaceutically necessary tableting excipients may be admixed with the granulate, e.g., via blending the ingredients together in a V-blender for a sufficient period of time to provide a smooth mixture, e.g., about 5 minutes. If desired, the mixture may then be compressed into tablets suitable for oral administration.

The mixture, in an amount sufficient to make a uniform batch of tablets, may then subjected to tableting in a conventional production scale tableting machine at normal compression pressure, e.g., about 2000–1600 lbs/sq in. However, the mixture should not be compressed to such a degree that there is subsequent difficulty in its hydration when exposed to gastric fluid.

Optionally, the tablets may be overcoated with a pharmaceutically acceptable film-coating, e.g., for aesthetic purposes (e.g., including a colorant), for stability purposes (e.g., coated with a moisture barrier), for taste-masking purposes, etc. For example, the tablets may be overcoated with a film coating, preferably containing a pigment and a barrier agent, such as hydroxypropylmethylcellulose and/or a polymethylmethacrylate. An example of a suitable material which may be used for such a hydrophilic coating is hydroxypropylmethylcellulose (e.g., Opadry®, commercially available from Colorcon, West Point, Pa.). In further embodiments of the present invention, the tablet coating may be comprised of an enteric coating material, alone or in combination with a hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material is sold under the trademark Eudragit™ L 100–555. Hydrophobic polymers capable of slowing the release rate of the active agent include derivatives of acrylic acid (such as esters of acrylic acid, methacrylic acid, and copolymers thereof) celluloses and derivatives thereof (such as ethylcellulose), polyvinylalcohols, and the like. Any pharmaceutically acceptable manner known to those skilled in the art may be used to apply the coatings. For example, the coating may be applied using a coating pan or a fluidized bed. An organic, aqueous or a mixture of an organic and aqueous solvent is used for the hydrophobic polymer or enteric coating. Examples of suitable organic solvents are, e.g., isopropyl alcohol, ethanol, and the like, with or without water. Aqueous solvents are preferred for the overcoating procedures. The optional coatings applied to the dosage form of the present invention may comprise from about 0.5% to about 30% by weight of the final solid dosage form.

Alternatively, the granulate may be incorporated into unit doses containing therapeutically effective amounts of paroxetine or sertraline, and the unit doses incorporated into gelatin capsules.

Some drugs exist in polymorphic forms, with different polymorphic forms exhibiting different bioavailability and/or physical properties (e.g., stability). The term "polymorphism" refers to different physical forms, such as crystalline forms or non-crystalline ("amorphous") forms. Paroxetine is an example of a drug that exhibits polymorphism.

The present invention is also directed to the preparation of amorphous paroxetine hydrochloride according to the processes disclosed above (e.g., preparing a solution in which paroxetine hydrochloride and a water-soluble polymer are dissolved in a co-solvent of a volatile organic solvent and water; and drying said solution to produce a composition comprising amorphous paroxetine hydrochloride and the water-soluble polymer) as well as obvious modifications known to those skilled in the art. The processes may be used to obtain a stable, substantially non-hygroscopic, amorphous form of paroxetine hydrochloride that is suitable for formulation into solid oral dosage forms, including immediate and sustained release dosage forms.

The procedure for obtaining a solid dispersion of amorphous paroxetine hydrochloride and polymer can be applied to obtain solid dispersions containing different amorphous salts of paroxetine or to obtain solid dispersions containing amorphous salts of sertraline.

DETAILED DESCRIPTION OF THE CERTAIN PREFERRED EMBODIMENTS

The following examples illustrate various aspects of the present invention. They are not to be construed to limit the claims in any manner whatsoever.

EXAMPLE 1

In Example 1, an oral solid dosage form containing amorphous paroxetine hydrochloride is prepared. The amorphous paroxetine hydrochloride is prepared by forming a solution in which paroxetine hydrochloride and a water-soluble polymer (e.g., polyvinylpyrrolidone) are dissolved in a co-solvent of a volatile organic solvent (e.g., methanol) and water, and drying said solution to obtain a composition comprising amorphous paroxetine hydrochloride and the water-soluble polymer. The composition is thereafter compressed into tablets.

1. Granulating (Paroxetine HCl Granules)

TABLE A

| Ingredient: | mg/tablet | % weight | kg |
|---|---|---|---|
| Paroxetine HCl, USP (Anhydrous) | 44.43 | 20.0 | 2.750 |
| Hydrochloric Acid, NF (37.6% w/w) | * | | 0.073 |
| Purified Water, USP | ** | | 7.352 |
| Methyl Alcohol, NF (Methanol) | ** | | 17.325 |
| Povidone K30, USP | 88.86 | 40.00 | 5.500 |
| Microcrystalline Cellulose, NF | 88.86 | 40.00 | 5.500 |
| (Avicel PH 101) | | | |
| Total: | 222.14 | 100.00 | 13.750 |

*10% excess of HCl (0.1:1 molar ratio to paroxetine) which will evaporate during granulation.
**Evaporated during granulation.

Paroxetine HCl Anhydrous, 2.75 kg, is dissolved in a co-solvent of methanol (17.325 kg) and water (7.352 kg) with 0.073 kg of hydrochloric acid. 5.50 kg of Povidone K30 is added to the solution and stirred until a clear solution is obtained. The solution is sprayed onto microcrystalline cellulose in a fluid bed processor with a Wuster apparatus at a temperature of 40–50° C. and a spray rate of 40–120 ml/min to form granules containing the solid dispersion of amorphous paroxetine in PVP. The granules are sized through a mill equipped with a 16 mesh screen to yield Paroxetine HCl Granules (amorphous).

2. Blending (Paroxetine HCl Blend)

TABLE B

| Ingredient: | mg/tablet | % weight | kg |
|---|---|---|---|
| Paroxetine HCl Granules (Amorphous) | 222.14 | 55.53 | 24.210 |
| Crospovidone, NF (Polyplasdone XL-10) | 40.00 | 10.00 | 4.360 |
| Microcrystalline Cellulose, NF (Avicel PH 102) | 135.89 | 33.97 | 14.810 |

TABLE B-continued

| Ingredient: | mg/tablet | % weight | kg |
|---|---|---|---|
| Magnesium Stearate, NF | 2.00 | 0.50 | 0.218 |
| Total: | 400.03 | 100.00 | 43.598 |

Paroxetine HCl Granules, 24.210 kg, are blended with 4.360 kg crospovidone, 14.810 kg microcrystalline cellulose and 0.218 kg magnesium stearate to yield a Paroxetine HCl Blend.

3. Tableting (Paroxetine HCl Tablets, 40 mg (Uncoated))

TABLE C

| Ingredient: | mg/tablet | % weight | kg |
|---|---|---|---|
| Paroxetine HCl Blend | 400.03 | 100.00 | 43.460 |

The Paroxetine HCl Blend is compressed into tablets with a tablet weight of 400 mg to yield Paroxetine HCl Tablets (core tablets).

4. Film Coating and Polishing (Paroxetine HCl Tablets, 40 mg (Coated))

TABLE D

| Ingredient: | mg/tablet | % weight | kg |
|---|---|---|---|
| Paroxetine HCl Tablet, 40 mg (Uncoated) | 400.03 | 96.97 | 42.430 |
| Opadry Pink, YS-1-14778A | 12.38 | 3.00 | 1.313 |
| Ethanol, SDA 3A 190 Proof | | | 11.812 |
| Candelilla Wax Powder, FCC | 0.12 | 0.03 | 0.013 |
| Total: | 412.53 | 100.00 | 43.756 |

The core tablets, 42.430 kg, are coated with a solution of 1.313 kg Opadry® Pink in 11.812 kg of ethanol using standard pan coating procedure. The film coated tablets are then polished by sprinkling 0.013 kg candelilla wax powder onto the tablets while the pan is rotating to yield Paroxetine HCl Tablets, 40mg (coated).

EXAMPLE 2

In Example 2, tablets containing amorphous paroxetine hydrochloride are prepared by dissolving paroxetine free base in a volatile organic solvent (e.g., methanol). Hydrochloric acid in water is then added to the paroxetine free base solution to form a solution of paroxetine hydrochloride in a co-solvent of a volatile organic solvent (e.g., methanol) and water. Subsequently, a water-soluble polymer (e.g., polyvinylpyrrolidone or "PVP") is added and the solution is sprayed onto a substrate (in this instance, microcrystalline cellulose) to produce granules containing a solid dispersion of paroxetine hydrochloride in PVP.

1. Preparation of 1N HCl (3.646% w/w) and Paroxetine HCl Solution

TABLE A
(Preparation of 1N HCl)

| Ingredient: | % weight | kg |
|---|---|---|
| Hydrochloric Acid, NF (10%) | 36.46 | 6.563 |
| Purified Water, USP | 63.54 | 11.437 |
| Total | 100.00 | 18.000 |

TABLE B (Preparation of Paroxetine HCl Solution)

| Ingredient: | mg/tablet | % weight | kg |
|---|---|---|---|
| Paroxetine Base | 40.00 | 89.15 | 5.000 |
| Hydrochloric Acid, NF (1 N, 3.646% w/w) | 4.43 | 10.85* | 0.609 (16.699 kg of 1 N HCl) |
| Methyl Alcohol, NF (Methanol) | * | | 34.113 |
| Total | 44.43 | 100.00 | 55.811 |

*containing 10% more HCl (1.1:1 molar ratio to paroxetine) which will evaporate during granulation and is not accounted for mg/tablet but for batch size and % weight.

Paroxetine Base, 5 kg, is dissolved in 34.1 kg of methanol and then 16.7 kg (1:1.1 molar ratio to paroxetine base) of 1N hydrochloric acid is added to the solution under stirring to yield paroxetine HCl solution in a co-solvent of methanol and water.

2. Granulating (Paroxetine HCl Granules)

TABLE C

| Ingredient: | mg/tablet | % weight | kg |
|---|---|---|---|
| Paroxetine HCl Solution, (10%, MeOH:H₂O = 70:30) | 44.43 | 20.0 | 2.777 |
| Povidone K30, USP (polyvinylpyrrolidone) | 88.86 | 40.0 | 5.553 |
| Microcrystalline Cellulose, NF (Avicel PH 101) | 88.86 | 40.0 | 5.553 |
| Total | 222.14 | 100.00 | 13.884 |

5.553 kg of Povidone K30 is added to 2.777 kg of Paroxetine HCl solution and stirred until a clear solution is obtained. The solution is sprayed onto 5.553 kg microcrystalline cellulose in a fluid bed processor with a Wuster apparatus at a temperature of 40–50° C. and a spray rate of 40–120 ml/min to form granules of a solid dispersion of amorphous paroxetine HCl in PVP. The granules are sized through a mill equipped with a 16 mesh screen to yield Paroxetine HCl Granules (amorphous).

The granules are then compressed into tablets after blending with other pharmaceutically acceptable excipients based on the procedure set forth in Example 1.

EXAMPLE 3

A solution of Paroxetine HCl in a co-solvent of methanol and water is prepared in accordance with the procedure set forth in Example 1 or Example 2. The prepared solution contains approximately 10% of paroxetine HCl (w/w). Next, a water-soluble polymer is added to the paroxetine HCl solution and stirred until clear solution is obtained. In Example 3A, the polymer added is polyvinylpyrrolindone (PVP), commercially available as Povidone K-30 or Povidone K-90. In Example 3B, the polymer added is hydroxypropylmethylcellulose (HPMC), preferably low viscosity grades of HPMC, e.g., HPMC commercially available as Methocel E5 or Methocel E3 LV, from Dow Chemical Co. In Example 3C, the polymer added is polyethyleneglycol (PEG), preferably PEG of MW of about 3,000 to 20,000. For each of Examples 3A–3C, the polymer is added until a drug to polymer ratio of 1:2, by weight, is achieved.

In Examples 3A–3C, the solution containing paroxetine hydrochloride and the water-soluble polymer is sprayed onto a substrate (in this instance, microcrystalline cellulose). The solution containing paroxetine hydrochloride and the water-soluble polymer is sprayed onto the microcrystalline cellulose in a fluid bed processor with a Wuster apparatus at a temperature of 40–50° C. and a spray rate of 40–120 ml/min to form granules.

A sufficient quantity of the paroxetine HCl granules, amounting to a suitable unit dose of paroxetine (e.g., 40 mg) may then be loaded into gelatin capsules. Alternatively, the paroxetine HCl granules are compressed into tablets, for example, in accordance with the procedures set forth in Example 1 or 2. The tablets may then be overcoated with a film coating for aesthetics (e.g., with a pigment) and/or for purposes of providing a moisture barrier, for example, in accordance with the procedures set forth in Example 1 or 2.

EXAMPLE 4

A solution of Paroxetine HCl in a co-solvent of methanol and water is prepared in accordance with the procedure set forth in Example 1 or Example 2. The prepared solution contains approximately 10% of paroxetine HCl (w/w). Next, a water-soluble polymer is added to the paroxetine HCl solution and stirred until clear solution is obtained. In Example 4A, the polymer added is polyvinylpyrrolindone (PVP), commercially available as Povidone K-30 or Povidone K-90. In Example 4B, the polymer added is hydroxypropylmethylcellulose (HPMC), preferably low viscosity grades of HPMC, e.g., HPMC commercially available as Methocel E5 or Methocel E3 LV, from Dow Chemical Co. In Example 4C, the polymer added is polyethyleneglycol (PEG), preferably PEG of MW of about 3,000 to 20,000. For each of Examples 4A–4C, the polymer is added until a drug to polymer ratio of 1:2, by weight, is achieved.

In Examples 4A–4C, the solution containing paroxetine hydrochloride and the water-soluble polymer is sprayed onto commercially available placebo tablets. Additional ingredients may be added to the solution before it is sprayed onto the placebo tablets to aid processing and/or stabilization. The procedure used to spray the paroxetine HCl onto the placebo tablets may employ techniques well known to those skilled in the art.

The tablets of Examples 4A–4C may then be overcoated with a film coating for aesthetics (e.g., with a pigment) and/or for purposes of providing a moisture barrier, for example, in accordance with the procedures set forth in Example 1 or 2.

EXAMPLE 5

A solution of Paroxetine HCl in a co-solvent of methanol and water is prepared in accordance with the procedure set forth in Example 1 or Example 2. The prepared solution contains approximately 10% of paroxetine HCl (w/w). Next, a water-soluble polymer is added to the paroxetine HCl solution and stirred until clear solution is obtained. In Example 5A, the polymer added is polyvinylpyrrolindone (PVP), commercially available as Povidone K-30 or Povidone K-90. In Example 5B, the polymer added is hydroxypropylmethylcellulose (HPMC), preferably low viscosity grades of HPMC, e.g., HPMC commercially available as Methocel E5 or Methocel E3 LV, from Dow Chemical Co. In Example 5C, the polymer added is polyethyleneglycol (PEG), preferably PEG of MW of about 3,000 to 20,000. For each of Examples 5A–5C, the polymer is added until a drug to polymer ratio of 1:2, by weight, is achieved.

In Examples 5A–5C, the solution containing paroxetine hydrochloride and the water-soluble polymer is spray dried according to conventional techniques well known to those skilled in the art. Additional ingredients may be added to the solution to aid processing and/or for stabilization before the spray drying procedure. Thereafter, the spray-dried product is compressed into tablets, adding excipients as necessary (e.g., a sufficient amount of a lubricant such as magnesium stearate; and a sufficient amount of a filler such as microcrystalline cellulose).

The tablets of Examples 5A–5C are then overcoated with a film coating for aesthetics (e.g., with a pigment) and/or for purposes of providing a moisture barrier, for example, in accordance with the procedures set forth in Example 1 or 2.

EXAMPLE 6

In Example 6, an oral solid dosage form containing amorphous sertraline hydrochloride is prepared similar to the oral solid dosage form containing amorphous paroxetine of Example 1. The amorphous sertraline hydrochloride is prepared by forming a solution in which sertraline hydrochloride and a water-soluble polymer (e.g., polyvinylpyrrolidone) are dissolved in a co-solvent of a volatile organic solvent (e.g., methanol) and water, and drying said solution to obtain a composition comprising amorphous sertraline hydrochloride and the water-soluble polymer. The composition is thereafter compressed into tablets.

The examples provided above are not meant to be exclusive. Many other variations of the present invention would be obvious to those skilled in the art, and are contemplated to be within the scope of the appended claims. For example, it will be recognized by those skilled in the art that a wide variety of pharmaceutically acceptable polymers may be utilized in the formulations of the invention, all of which are contemplated to be within the scope of the appended claims. Further, a wide variety of pharmaceutical excipients may be added for their intended purpose, depending upon the particular type of final formulation being prepared, as described herein.

What is claimed is:

1. A process for preparing a solid dispersion comprising an active ingredient and a water-soluble polymer, said process comprising:
   (a) preparing a solution in which an active ingredient and a water-soluble polymer are dissolved in a co-solvent of a volatile organic solvent and water, wherein the active ingredient is a selective aerotonin reuptake inhibitor and a weight ratio of said volatile organic solvent to said water is from about 95:5 to about 60:40; and
   (b) drying said solution to produce a solid dispersion comprising the active ingredient dispersed in the water-soluble polymer; said drying comprising spray-drying the solution of step (a) onto a pharmaceutically acceptable carrier.

2. The process of claim 1, wherein the active ingredient is paroxetine hydrochloride or sertraline hydrochloride.

3. The process of claim 2, wherein the active ingredient is paroxetine hydrochloride.

4. The process of claim 1, wherein the active ingredient is an acid addition salt of paroxetine or an acid addition salt of sertraline, and the solution, when dried, produces a solid dispersion comprising amorphous form of the active ingredient dispersed in the water-soluble polymer.

5. The process of claim 1, wherein the active ingredient is paroxetine hydrochloride or sertraline hydrochloride, and the solution, when dried, produces a solid dispersion comprising amorphous paroxetine hydrochloride or amorphous sertraline hydrochloride dispersed in the water-soluble polymer.

6. The process of claim 5, wherein the active ingredient is paroxetine hydrochloride and the preparation of the solution of step (a) comprises: dissolving paroxetine free base in a volatile organic solvent to form a solution of paroxetine free base; adding hydrochloric acid dissolved in water to said paroxetine free base solution, the amount of said hydrochloric acid being sufficient to ensure conversion of said paroxetine free base to paroxetine hydrochloride, to form a solution in which paroxetine hydrochloride is dissolved in a co-solvent of the volatile organic solvent and water; and adding a water-soluble polymer into the paroxetine hydrochloride solution to form a solution in which the water soluble polymer and paroxetine hydrochloride are dissolved in the co-solvent.

7. The process of claim 5, wherein the active ingredient is paroxetine hydrochloride and the preparation of the solution of step (a) comprises dissolving paroxetine hydrochloride in a co-solvent of a volatile organic solvent and water; and adding to said paroxetine hydrochloride solution a water-soluble polymer to form a solution in which paroxetine hydrochloride and the water-soluble polymer are dissolved in the co-solvent.

8. The process of claim 5, wherein the weight ratio of the volatile organic solvent to water in step (a) is about 80:20 to about 70:30.

9. The process of claim 5, wherein the concentration of paroxetine hydrochloride or sertraline hydrochloride in step (a) is from about 2% to about 30%, by weight.

10. The process of claim 5, wherein the weight ratio of the active ingredient to the water-soluble polymer is from about 1:1 to about 1:4.

11. The process of claim 5, wherein the concentration of the active ingredient in step (a) is from about 5% to about 25%, by weight.

12. The process of claim 5, wherein the weight ratio of the active ingredient to the water-soluble polymer is from about 1;1 to 1:2.

13. The process of claim 5, wherein the amount of the water soluble polymer in the solution of step (a) is sufficient to prevent recrystallization of the active ingredient.

14. The process of claim 13, wherein the amount of the water soluble polymer in the solution of step (a) is not more than about 30% by weight.

15. The process of claim 5, wherein the water soluble polymer is selected from the group consisting of polyvinylpyrrolidone, hydroxypropylmethylcellulose, polyethylene glycol and mixtures thereof, the water soluble polymer comprising about 20% of the solution of step (a) by weight.

16. The process of claim 5, wherein the water-soluble polymer comprises polyvinylpyrrolidone having an average molecular weight of from about 7,000 to about 1,500,000.

17. The process of claim 5, wherein the volatile organic solvent is selected from the group consisting of isopropyl alcohol, methanol, ethanol and mixtures thereof.

18. The process of claim 5, wherein the volatile organic solvent is methanol.

19. The process of claim 1, wherein the solution of step (a) is sprayed onto the pharmaceutically acceptable carrier to a weight gain of from about 5% to about 500%.

20. The process of claim 1, wherein the solution of step (a) is sprayed onto the pharmaceutically acceptable carrier to a weight gain of from about 50% to about 300%.

21. The process of claim 20, wherein the solution of step (a) is spray dried onto the pharmaceutically acceptable carrier to produce granules comprising amorphous paroxetine hydrochloride or sertraline hydrochloride, the water-soluble polymer, and the pharmaceutically acceptable carrier.

22. The process of claim 20, wherein the pharmaceutically acceptable carrier is selected from the group consisting of microcrystalline cellulose, calcium phosphate dibasic, calcium phosphate dihydrate, calcium sulfate dihydrate, cellulose derivatives, dextrose, lactose, anhydrous lactose, spray-dried lactose, lactose monohydrate, mannitol, starches, sorbitol, sucrose, hydroxypropylmethylcellulose, hydroxypropylcellulose, methylcellulose, carboxymethylcellulose, sodium carboxymethylcellulose, polyvinylpyrrolidone, polyethyleneglycol, cellulose acetate butyrate, hydroxyethylcellulose, ethylcellulose, polyvinyl alcohol, polypropylene, dextrans, dextrins, hydroxypropyl-beta-cyclodextrin, chitosan, copolymers of lactic and glycolic acid, lactic acid polymers, glycolic acid polymers, polyorthoesters, polyanyhydrides, polyvinyl chloride, polyvinyl acetate, ethylene vinyl acetate, lectins, carbopols, silicon elastomers, polyacrylic polymers, maltodextrins, fructose, inositol, trehalose, maltose raffinose, and alpha-, beta-, and gamma-cyclodextrins, and mixtures thereof.

23. The process of claim 1, further comprising the step of spray coating the solution of step (a) onto a placebo tablet.

24. The process of claim 5, wherein the process further comprises addition of at least one pharmaceutically acceptable excipient into the solution of step (a) before the drying step.

25. The process of claim 24, wherein the pharmaceutical excipient is selected from the group consisting of a surfactant, a stabilizer, an antioxidant, a glidant, and mixtures thereof.

26. The process of claim 21, further comprising admixing to the granules a sufficient quantity of at least one pharmaceutically acceptable tableting excipient, and compressing said mixture into tablets suitable for oral administration.

27. The process of claim 26, further comprising the step of overcoating said tablets with a pharmaceutically acceptable film-coating.

28. The process of claim 26, wherein the pharmaceutically necessary tableting excipient is selected from the group consisting of a lubricant, an inert filler, a glidant, a disintegrant and mixtures thereof.

29. The process of claim 5, further comprising the step of formulating the solid dispersion comprising the amorphous form of the active ingredient into a dosage form suitable for oral administration.

30. The process of claim 29, wherein the dosage form is a controlled-release dosage form.

31. The process of claim 29, wherein the dosage form is an immediate-release dosage form.

32. The product obtained by the process of claim 1.

33. The process of claim 1, further comprising adding a stabilizer into said solution prior to said drying.

34. The process of claim 33, wherein said stabilizer is a pharmaceutically acceptable inorganic or organic acid.

35. The process of claim 34, wherein said acid is the same acid as the acid addition portion of the active ingredient.

36. The process of claim 34, wherein said acid is hydrochloric acid.

37. The process of claim 33, wherein said stabilizer is added to said co-solvent prior to the addition of the active ingredient and the water soluble polymer.

38. The product obtained by the process of claim 33.

39. A pharmaceutical composition comprising: a solid dispersion of an amorphous form of an acid addition salt of paroxetine; and a water soluble polymer; said pharmaceutical composition prepared by
  (a) preparing a solution in which said acid addition salt of paroxetine and said water-soluble polymer are dissolved in a co-solvent of a volatile organic solvent and water, wherein a weight ratio of said volatile organic solvent to said water is from about 95:5 to about 60:40; and
  (b) drying said solution to produce a solid dispersion comprising the amorphous form of said acid addition salt of paroxetine dispersed in said water-soluble polymer; said drying comprising spray-drying the solution of step (a) onto a pharmaceutically acceptable carrier.

40. The pharmaceutical composition of claim 39, wherein said solid dispersion has a weight ratio of said amorphous form of an acid addition salt of paroxetine to said water soluble polymer of from about 1:1 to about 1:4.

41. The pharmaceutical composition of claim 39, further comprising a stabilizer.

42. The pharmaceutical composition of claim 41, wherein said stabilizer is an inorganic or organic acid.

43. The pharmaceutical composition of claim 41, wherein said stabilizer is an inorganic or organic acid which is the same acid as the acid addition portion of said acid addition salt of paroxetine.

44. The pharmaceutical composition of claim 43, wherein said same acid is hydrochloric acid.

45. A pharmaceutical composition comprising:
  a solid dispersion comprising
    (a) an active ingredient selected from the group consisting of paroxetine free base, an acid addition salt of paroxetine, sertraline free base and an acid addition salt of sertraline; and
    (b) a water-soluble polymer; wherein said solid dispersion is prepared by drying a solution in which said active ingredient and said water-soluble polymer are dissolved in a co-solvent of a volatile organic solvent and water, wherein a weight ratio of said volatile organic solvent to said water is from about 95:5 to about 60:40 and said drying comprises spray-drying the solution onto a pharmaceutically acceptable carrier.

46. A process according to claim 1, wherein the selective serotonin reuptake inhibitor is selected from the group consisting of paroxetine free base, an acid addition salt of paroxetine, sertraline free base and an acid addition salt of sertraline.

* * * * *